United States Patent [19] [11] 4,419,210
Wang [45] Dec. 6, 1983

[54] POLAROGRAPHIC ELECTRODE

[75] Inventor: Minchen Wang, Bayside, N.Y.

[73] Assignee: Photovolt Corporation, Midland, Mich.

[21] Appl. No.: 406,687

[22] Filed: Aug. 9, 1982

[51] Int. Cl.³ .......................................... G01N 27/54
[52] U.S. Cl. ................................. 204/403; 128/635; 204/412; 204/415; 435/817
[58] Field of Search ............... 204/403, 412, 415, 1 P, 204/411; 128/635; 435/817

[56] References Cited

U.S. PATENT DOCUMENTS 3,539,455 11/1970 Clark .................................... 204/1 T
3,867,273 2/1975 Gilbert ................................ 204/400
4,073,713 2/1978 Newman ............................. 204/403

Primary Examiner—G. L. Kaplan
Attorney, Agent, or Firm—Burke M. Halldorson; Paul J. Cook

[57] ABSTRACT

An improved 3-pole membrane electrode for polarographic measurements in which an auxiliary electrode is defined having an arc which is generated by rotation about the center point of a disc-shaped working electrode. A preferable liquid junction form of reference electrode is located in the sector defined by the arc of the auxiliary electrode and the center point of the working electrode; and an analyte permeable membrane is intimately conformed over the sensing face of the improved polarographic electrode.

10 Claims, 3 Drawing Figures

POLAROGRAPHIC ELECTRODE

BACKGROUND OF THE INVENTION

This invention relates to a polarographic membrane electrode of the general type described by Newman in U.S. Pat. No. 4,073,713, and the various references incorporated by Newman in this teaching. These membrane electrodes are used, e.g., in clinical analyzers such as described by Gilbert in U.S. Pat. No. 3,867,273, also incorporated by reference.

There particularly exists a need for improved membrane electrodes for polarography which are compact in geometry and which are generally less sensitive to interferences, e.g., as described by Clark in U.S. Pat. No. 3,539,455, also incorporated by reference.

BRIEF SUMMARY OF THE INVENTION

This invention is an improved membrane electrode which is compact and substantially overcomes prior chloride ion interferences and other common interferences, e.g. as caused by acetamidophenol (Tylenol) in the analysis of human serum samples.

The improved polarographic membrane electrode comprises an analyte permeable membrane conformed to a surface of a solidified filler matrix of an insulator material, which surface is further comprised of the exposed surfaces of embedded electrodes which are coincident with the adjacent surface of the filler matrix, the electrodes comprising an auxiliary electrode, working electrode, and reference electrode, the geometry of the auxiliary electrode defining a critical boundary which is an arc generated from a radius rotated about a point which is the center of the working electrode, the reference electrode being in the sector defined by the arc of the auxiliary electrode and the center of the working electrode.

The improved electrode is particularly developed for use in polarographic measurements based on using oxireductase enzymes immobilized in membrane structures to react with analyte of interest to yield polarographically determinable $H_2O_2$.

THE DRAWING

Yet further objectives, aspects and advantages of the invention will in part be pointed out and in part apparent from the following detailed description considered together with the Drawing wherein.

DETAILED DESCRIPTION OF THE INVENTION

Figure 1:
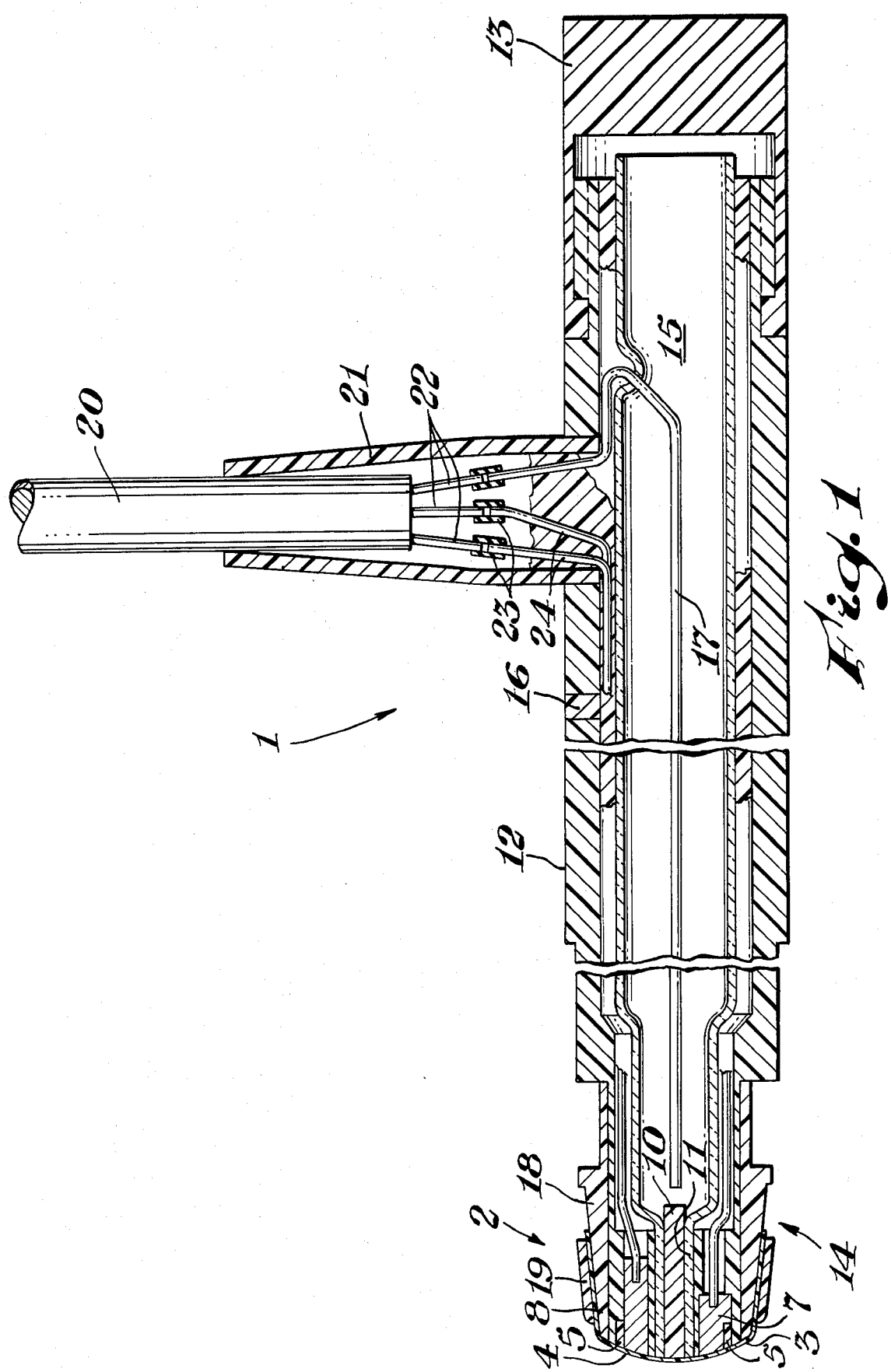
FIG. 1 is an enlarged, cross-sectional view of a polarographic membrane electrode which is a preferred embodiment constructed in accordance with the teachings and principles of this invention.
Figure 3:
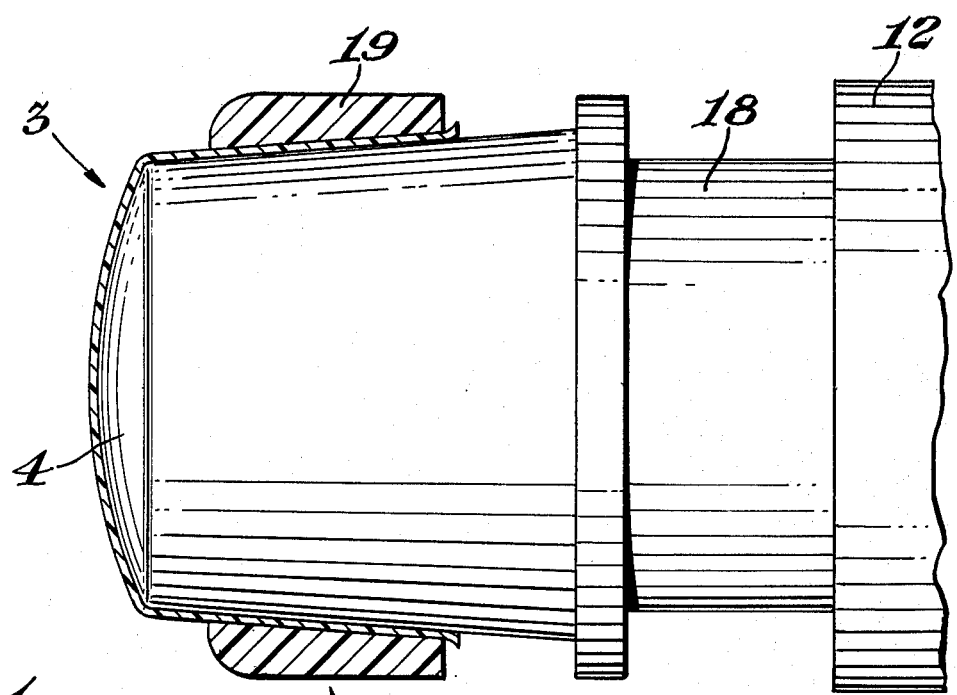
FIG. 3 is an end view of the sensing face of the electrode of FIG. 1 illustrating the three-electrode design and generally the relationships between the electrodes necessary for proper performance.

Referring now to the Drawing, a polarographic membrane electrode or electrode probe 1 is illustrated which is of generally elongated cylindrical geometry; and which includes a sensing head or end portion 2. The sensing end portion 2 comprises an analyte permeable membrane 3 which is conformed intimately to a generally convex, smooth surface comprising a probe sensing face 4. The sensing face 4 is comprised of the polished surface of a solidified filler matrix 5 of an electrical insulator material. The sensing face 4 is further comprised of the polished and exposed surfaces of electrodes 6, 7 and 8 which are embedded in filler matrix 5. The exposed surfaces of electrodes 6, 7 and 8 are generally coincident with the exposed surface of the filler matrix, and preferably coplanar therewith. These surfaces comprising the sensing face 4 are additionally preferably exactly conformed to membrane 3 such that no appreciable space or gap exists between sensing face 4 and the inside of the membrane.

The electrodes more specifically comprise a crescent-shaped auxiliary electrode, which is the electrode 6; a disc-shaped working electrode which is the electrode 8; and a second disc-shaped electrode, designated as the electrode 7, and which is the reference electrode. The boundary of auxiliary electrode 6 defines an arc 9 which is coincident with that which is generated from an imaginary radius (radius "r" which is shown in dotted lines in FIG. 2) rotated about a point which is the center point of the working electrode. In addition, the position of the reference electrode 7 vs. electrodes 6 and 8 is critically defined. This critical positioning is satisfied whenever the reference electrode is located in the imaginary sector defined by the arc of the auxiliary electrode and the imaginary center point of the working electrode. This sector is shown in FIG. 2 by dotted lines "s".

Figure 2:
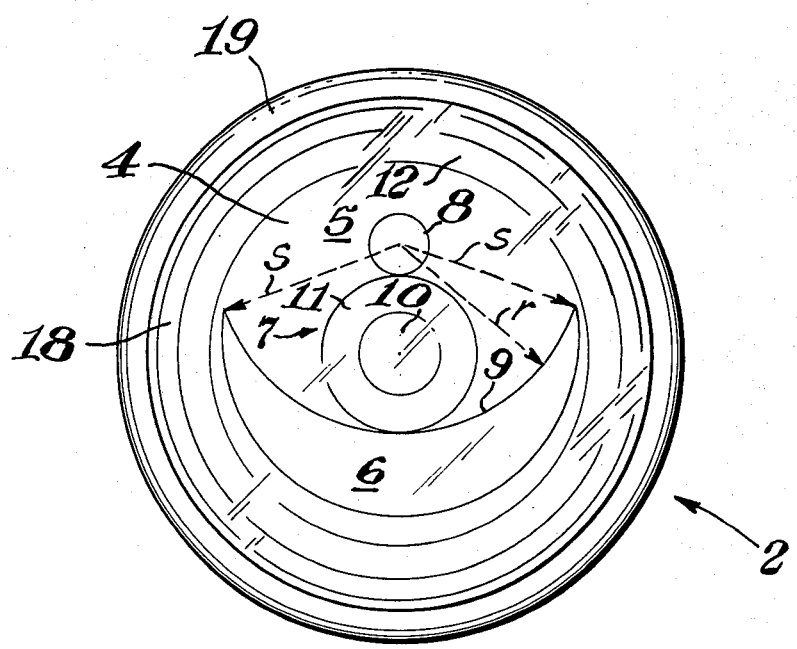
FIG. 2 is an enlarged view of the membrane retaining assembly of the electrode of FIG. 1.

The reference electrode of the membrane probe 1 is preferably comprised of a liquid junction formed such as by a liquid porous element or frit 10 contained within an insulator sleeve 11, e.g., of glass (see FIG. 2). Most desirably the glass sleeve 11 is in contact or very close spacing with both the working electrode and auxiliary electrode. This design is advantageous since it places the reference electrode in a position of minimum resistance vs. the working electrode; and additionally allows the surface area of the auxiliary electrode to be maximized vs. the working electrode. Most desirably, the polarographic membrane electrode of this invention is designed in accordance with the further requirement that:

$$(A_{Aux}/A_{W.E.}) \geq 5$$

where $A_{Aux}$ is the surface area of the auxiliary electrode and $A_{W.E.}$ is the surface area of the working electrode.

A polarographic membrane electrode 1 made in accordance with the above criteria may take various design forms, but a highly preferred design is that illustrated in detail in FIG. 1. This design includes a hollow plastic body, which is formed of several components comprising a central body portion 12; threaded cap closure 13; and a membrane retainer assembly 14 attached to the opposite (non-threaded) end of central body portion 12. Inserted within body portion 13 is a glass envelope 15, preferably of borosilicate glass, which is necked down in steps to form a narrow diameter sleeve (previously designated glass sleeve 11) in which is contained a frit, e.g., of zirconium oxide, or an equivalent frit which forms the required liquid junction. The space between the glass envelope 15 and hollow plastic body is filled with, e.g. RTV silicone rubber sealant 16 added, e.g., by injection through a drilled opening in central body portion 12. This forms an annular seal between the envelope and central body portion, whereby electrolyte solution is conveniently added to the glass envelope through threaded cap closure 13. Contained within the glass envelope is a wire 17 (reference electrode) of, e.g., Ag/AgCl which exits through an opening in the glass envelope and is ultimately connected to a shielded cable as will be described more fully hereinafter. Various other forms of reference electrodes may be used for the polarographic membrane electrode 1, e.g., a saturated calomel reference electrode may be alternatively employed.

The working electrode 8 is preferably of a noble metal such as platinum and the auxiliary electrode 6 is preferably of pure silver metal. These contact the glass sleeve 11 of the reference electrode, at the points shown in FIG. 2, with the spaces not occupied by the electrodes 6, 7 and 8, occupied by an insulator matrix, previously designated as the filler matrix 5. The filler matrix 5 can be formed, e.g., of an epoxy resin, such as for illustrative example only, STYCAST® No. 2057 epoxy resin.

Membrane retainer assembly 14 comprises a cap element 18 which is cylindrical, and is pressure fitted about the sensing end 2 of the membrane electrode 1. A ring 19 is pressure fitted to cap 18 to retain membrane 3 intimately against sensing face 4. The cap element 18 and ring 19 are removable to permit replacement of membranes which employ, e.g., an immobilized enzyme which is depleted with use. This type of membrane (without intention of limiting this teaching to any specific polarographic membrane) typically includes an enzyme incorporated as an adhesive layer sandwiched between analyte permeable membrane layers; and which layered membrane is constructed, e.g., according to U.S. Pat. No. 4,073,713 incorporated fully herein by reference.

The membrane electrode 1 is preferably operated using shielded twisted pair cable 20. The cable is fastened in a sleeve 21 fixed to central body portion 13; and the cable leads 22 are joined preferably by soldered joints 23 to electrical lead wires 24, in turn connected, e.g., by soldered joints to the Ag/AgCl electrode, working electrode and auxiliary electrode, respectively.

The membrane electrode 1 of the invention has utility broadly for determining analytes in solution wherein generally a membrane is chosen which is permeable to the analyte to be measured and impermeable to interferring solute; and/or is chosen in order to determine polarographically electroinactive analyte of interest by detecting reaction products of such analytes which are permeated and are suitably electro-active. The membrane electrode is particularly considered useful in connection with determining analytes which react with oxi-reductase enzymes immobilized on membranes.

EXAMPLE 1

Linearity

Membrane electrodes designed according to the invention are evaluated which comprise as the membrane, a three layered laminate of cellulose/immobilized glucose oxidase/cellulose acetate; the total membrane thickness being less than about 50 microns. These electrodes employ an Ag/AgCl reference electrode immersed in a 0.3 molar NaCl electrolyte solution. Sample standards of various concentrations of glucose are prepared for testing using as the diluent, a solution of 0.075 molar triethanolamine (TEA) diluent. The following Table shows the linearity of the glucose measurement (measuring evolved $H_2O_2$) of various test solutions.

TABLE

| Test Solution | Glucose Conc. Mg/dl | Measured Glu. Conc. Mg/dl |
|---|---|---|
| A | 50 | 48.25 ± 2.21 |
| B | 100 | 98.50 ± 1.29 |
| C | 150 | 146.75 ± 2.98 |
| D | 250 | 254.5 ± 5.74 |
| E | 325 | 319.8 ± 3.40 |
| F | 400 | 409.0 ± 6.27 |

An important feature of the tested membrane electrode of the invention is that the linearity line intercepts the axis at about 0 mg/dl. Thus linearity at low concentrations is observed; a result not always true with prior art 2-pole polarographic membrane electrodes.

EXAMPLE 2

Chloride Ion Interference

The membrane electrode of the invention responds to chloride ion concentration variations only minimally. These are measured by measuring the chloride ion dependence coefficient (C.D) of the electrode which is defined as:

$$C.D. = \frac{\Delta I}{\Delta [Cl]} \times \frac{200 \text{ mg/dl}}{I \text{ glucose, 200 mg/dl}}$$

where
$\Delta I$ = current difference caused by chloride concentration variation
$\Delta[cl]$ = chloride concentration variation in the test solutions.

In order to measure C.D., various solutions are prepared to cover the chloride range 50~160 (meg/l in 0.075 molar TEA diluent). The glucose concentration in all test solutions is 100 mg/dl.

The highest C.D. determined from these test solutions is only 0.091 using membrane electrodes constructed according to the invention. A C.D. of less than 0.1 implies that the glucose measurement error is less than ±3.0 mg/dl for the entire range of chloride concentrations tested.

EXAMPLE 3

Acetamidophenol (Tylenol) Interferences

Test solutions comparable to human serum are diluted in 0.075 molar TEA diluent (approximately neutral pH). These solutions are prepared which contain 60 Mg/dl glucose and 10 Mg/dl acetamidophenol. The interference of the latter compound is avoided by using an operating voltage of about −390 mV of the working electrode vs. the reference electrode. Glucose response at this voltage is reduced only minimally. In addition, the electrode is operated with excellent stability.

What is claimed is:
1. A membrane electrode comprising an analyte permeable membrane conformed to a smooth surface of a solidified filler martrix of an insulator material, which smooth surface is further comprised of the exposed surfaces of embedded electrodes which are flush with the adjacent surface of the filler matrix, the electrodes comprising an auxiliary electrode, working electrode, and reference electrode, the geometry of the auxiliary electrode defining a critical boundary which is an arc generated from a radius rotated about a point which is the center of the working electrode, the reference electrode being in the sector defined by the arc of the auxiliary electrode and the center of the working electrode.

2. The membrane electrode of claim 1 in which the reference electrode at its exposed surface with the filler matrix comprises an element forming a liquid junction.

3. The membrane electrode of claim 2 in which said reference electrode is juxtaposed with the auxiliary and working electrodes, respectively.

4. The membrane electrode of claim 3 in which the working electrode comprises a noble metal.

5. The membrane electrode of claim 4 comprising as the reference electrode, a Ag/AgCl electrode.

6. The membrane electrode of claim 5 in which the filler matrix comprises a cured epoxy.

7. The membrane electrode in claim 4 comprising as the reference electrode, a saturated calomel electrode.

8. The membrane electrode of claim 1 in which the electrode is designed such that $$(A_{Aux}/A_{W.E.}) \geq 5.$$

9. The membrane electrode of claim 8 in which the geometry of the auxiliary electrode is cresentshaped; and the geometry of the working electrode is a disc.

10. The membrane electrode of claim 1 in which the membrane comprises immobilized glucose oxidase enzyme sandwiched between analyte permeable film membrane layers.

* * * * *